US006397104B1

(12) United States Patent
Miller et al.

(10) Patent No.: US 6,397,104 B1
(45) Date of Patent: May 28, 2002

(54) DEFIBRILLATION SYSTEM HAVING DEFIBRILLATOR WITH REPLACEABLE SUPPLY MODULE

(75) Inventors: James L. Miller, Westford, MA (US); James Daren Bledsoe, Albany, OR (US); Helge Fossan; Arild J. Eikefjord, both of Stavanger (NO)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/354,182

(22) Filed: Jul. 16, 1999

(51) Int. Cl.[7] .................................................. A61N 1/39
(52) U.S. Cl. ......................................................... 607/5
(58) Field of Search ................................. 607/1, 2, 4, 5, 607/10, 36, 37

(56) References Cited

U.S. PATENT DOCUMENTS

| 4,097,113 A | * | 6/1978 | McKelvy ........................ 607/5 |
| 5,658,316 A | * | 8/1997 | Lamond et al. ................. 607/5 |
| 5,697,955 A | | 12/1997 | Stolte |
| 5,700,281 A | | 12/1997 | Brewer et al. |
| 6,128,530 A | * | 10/2000 | Galen et al. .................... 607/5 |
| 6,148,233 A | * | 11/2000 | Owen et al. .................... 607/5 |

* cited by examiner

Primary Examiner—George R. Evanisko

(57) ABSTRACT

A defibrillation system includes an automatic external defibrillator and a supply module containing items for use in connection with the automatic external defibrillator. The supply module may be physically coupled to the defibrillator to ensure the availability of the items during operation of the defibrillator. Items within the supply module or the supply module itself may also be electrically coupled to the defibrillator to reduce the amount of time required to deploy the defibrillator when responding to an emergency medical situation. Items containable by the supply module include pads, ECG leads, gloves, scissors, PCMCIA cards and defibrillator batteries, as well as any other components or supplies desired to be included by the operator or manufacturer. The supply module may be provided with a visible or electronically readable indicia of the shelf life of the supply module or one or more items contained by the supply module. Memory or other circuitry may be provided on the supply module to communicate with the defibrillator prior to, during or after operation of the defibrillator to facilitate exchanges of information between the supply module, defibrillator, defibrillator operator and defibrillator maintenance personnel.

18 Claims, 3 Drawing Sheets

DEFIBRILLATION SYSTEM HAVING DEFIBRILLATOR WITH REPLACEABLE SUPPLY MODULE

BACKGROUND OF THE INVENTION

1. Field of the Invention

The present invention relates generally to a portable external defibrillator and, more particularly, to an accessory for a portable external defibrillator.

2. Related Art

Sudden cardiac arrest is a disruption of the heart's functioning that causes a lack of blood flow to vital organs. In a majority of instances, sudden cardiac arrest is manifested as an abnormal or chaotic heart rhythm, called fibrillation. These instances are generally identifiable by the victim's immediate loss of pulse, loss of consciousness and a cessation of breathing.

Sudden cardiac arrest has been attributed to over 350,000 deaths each year in the United States, making it one of the country's leading medical emergencies. World-wide, sudden cardiac arrest has been attributed to a much larger number of deaths each year. Unless immediate medical intervention is initiated, sudden cardiac arrest can lead to death within a matter of minutes.

There are four critical components of medical treatment that must be administered to a victim of sudden cardiac arrest: (1) early access to emergency care; (2) early cardiopulmonary resuscitation to keep the blood oxygenated and flowing to the victim's brain and other vital organs; (3) early defibrillation (the application of an electrical shock to the heart) to restore the heart's regular rhythm; and (4) early access to advanced medical care. When a person is experiencing sudden cardiac arrest, the electrical activity within the heart becomes chaotic. An electric shock from a defibrillator can reorganize the electrical impulses to allow coordinated pumping action to resume. To administer this shock, special pads from a machine called a defibrillator are placed on the victim's chest, and an electric shock is sent through the victim's body from one pad to another. As used herein, the term "pads" will include both pads and paddles.

If prompt cardiopulmonary resuscitation is followed by defibrillation within about four minutes, the victim's chances of surviving sudden cardiac arrest can approach or exceed fifty percent. Prompt administration of defibrillation within the first critical minutes is considered one of the most important components of emergency medical treatment for preventing death from sudden cardiac arrest.

Since prompt defibrillation is critical to survival, portable defibrillators have been developed that can be carried to the victim's location to defibrillate the victim prior to reaching a hospital. Also, there is a trend to place portable defibrillators in areas of hospitals not generally staffed with emergency personnel and in other public areas where difficult to reach patients are likely to be encountered, such as airplanes, airports, cruise liners, casinos, sports arenas and other populous facilities that are difficult or time consuming to access.

Automatic external defibrillators are typically used rather infrequently. Indeed, it has been estimated that a defibrillator will typically not be used more often than once every one to two years. To ensure that the defibrillator is operational, each conventional defibrillator periodically performs a test procedure to ensure the viability of its circuits. If any defect is detected, an alarm or other indication will be provided to the owner/operator of the defibrillator indicating that service is required. Optionally, the alarm may be communicated to a remote monitoring location over a network, by telephone, etc.

Various supplies are required to operate a defibrillator. Typically, automatic external defibrillators make use of either pre-connected or user attached self-adhesive pads. A gel conductor is provided in the center of each self-adhesive pad to provide a reliable contact between the victim's skin and wires connected to the pads. The gel on the pads may dry over time, reducing the effectiveness of the pads and limiting the effective shelf-life of the pads to approximately two years.

Likewise, batteries provided to operate the defibrillator must be recharged or replaced when depleted. The shelf life of a battery, depending on the battery chemistry, is typically around five years.

Maintenance of a fleet of defibrillators is thus complicated by the numerous items necessary for operation of the defibrillator that must be monitored in addition to monitoring the operational status of the defibrillator itself. Accordingly, it would be advantageous to provide a system whereby the status of the defibrillator and items associated with operation of the defibrillator could be monitored easily.

SUMMARY OF THE INVENTION

The present invention relates to a defibrillation system that includes an automatic external defibrillator and a supply module containing items for use in connection with the automatic external defibrillator. The supply module may contain many items, including pads, ECG leads, gloves, CPR barrier masks, scissors, PCMCIA cards and batteries for the defibrillator, as well as any other components or supplies desired to be included by the operator or manufacturer. The supply module typically is physically coupled to the defibrillator to ensure the availability of the items during operation of the defibrillator. Items within the supply module such as the battery and pads or the supply module itself may be electrically coupled to the defibrillator to reduce the amount of time required to deploy the defibrillator when responding to an emergency medical situation. In another aspect of the invention, the supply module may be provided with a visible or electronically readable indicia of the shelf life of the supply module or one or more items contained by the supply module. A memory or other circuitry may be provided on the supply module to communicate with the defibrillator prior to, during or subsequent to operation of the defibrillator to facilitate exchanges of information between the supply module, defibrillator, defibrillator operator and defibrillator maintenance personnel.

In one embodiment, a defibrillation system includes an external defibrillator and a replaceable supply module, including pads and a battery, mounted on the external defibrillator. In this embodiment, the replaceable supply module may be physically or electrically connected to the external defibrillator. The replaceable supply module may be a container with compartments to contain the pads and battery. The container may have a peelable top surface, and may be configured such that operation of the defibrillator is initiated by peeling the peelable top surface. The replaceable supply module has an expiration date, which may be the earlier of an expiration date of the pads and an expiration date of the battery. The expiration date may take on many forms, such as visible indicia printed on an surface of the replaceable supply module, or indicia in machine-readable form readable by the defibrillator. When the expiration date is in machine readable form, the defibrillator is able to monitor the expiration date and communicate information regarding the expiration date locally or remotely.

In another aspect, the defibrillator is configured to conduct a periodic test of the replaceable supply module in connection with or separate from periodic self tests. The results of the periodic tests of the replaceable supply module are communicated locally or remotely by the defibrillator display or communication unit respectively. The defibrillator may be configured to compare the expiration date of the supply module with the current date, and to issue at least one of an audible and visual warning indicating that the supply module has passed its expiration date or is approaching its expiration date.

In another embodiment, the defibrillation system includes a defibrillator configured to monitor a supply module and a supply module containing pads and a battery electrically connectable to the defibrillator. The supply module may also contain ECG leads, gloves, a CPR barrier mask, a PCMCIA memory card, scissors and a memory. The memory is configured to store information for transmission from the supply module to the defibrillator, such as information related to the expiration date of the supply module, expiration dates of items contained by the supply module, training scenarios, codes necessary for operation of the defibrillator or software and algorithms usable by the defibrillator during the defibrillation process. Likewise, the supply module may contain a memory configured to store information received from the defibrillator, such as ECG data, event data and audio data.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

DETAILED DESCRIPTION

Figure 1:
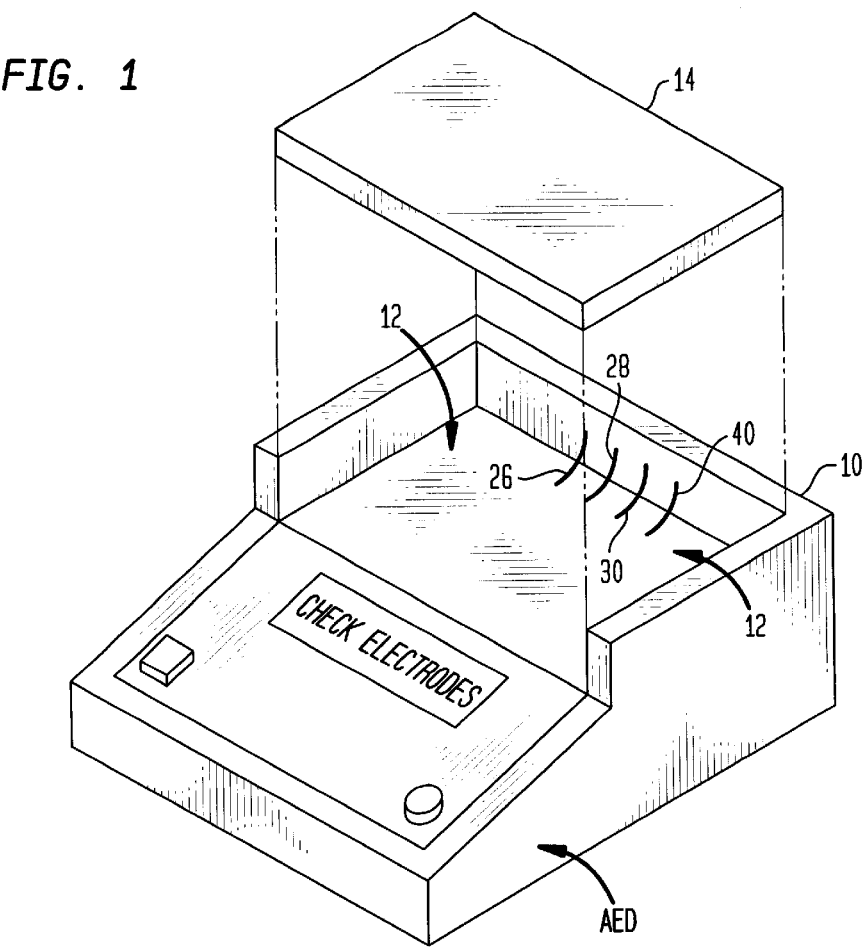
FIG. 1 is perspective view of a defibrillator according to one embodiment of this invention.

With reference to FIG. 1, the present invention will now be described. A defibrillation system 8 includes an external defibrillator 10 having a supply module 14 containing items for use in connection with the external defibrillator 10. As a battery-powered device, the defibrillator 10 is highly portable and therefore suitable for pre-hospital (emergency) use. The supply module 14 may be any container, holder, receptacle, vessel, box, carton or other device able to contain, connect, retain, collect, or otherwise hold (collectively contain) items for use in connection with operation of the defibrillator 10 or items usable to operate the defibrillator 10. The supply module preferably is physically coupled to the defibrillator to ensure the availability of the items during operation of the defibrillator such as by a socket 12.

A mechanical latch, magnet, cord or other device capable of physically coupling the supply module to the defibrillator may be used to retain the supply module 14 within the socket 12. Optionally, the supply module may be physically coupled to the defibrillator via an intermediary structure, such as by being retained in a pocket or other compartment of the defibrillator's carrying case.

Figure 2:
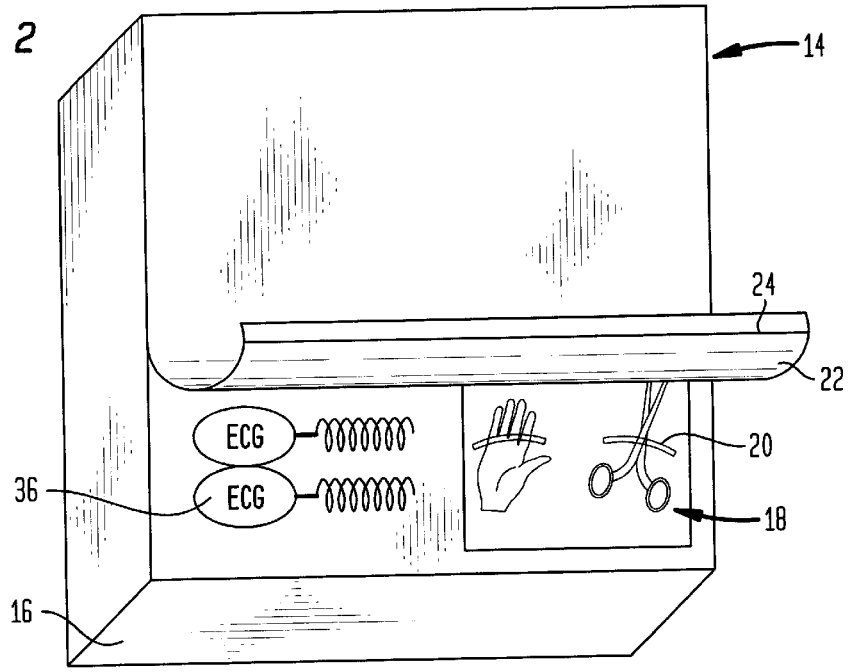
FIG. 2 is a perspective view of a module for use with the defibrillator of FIG. 1.
Figure 3:
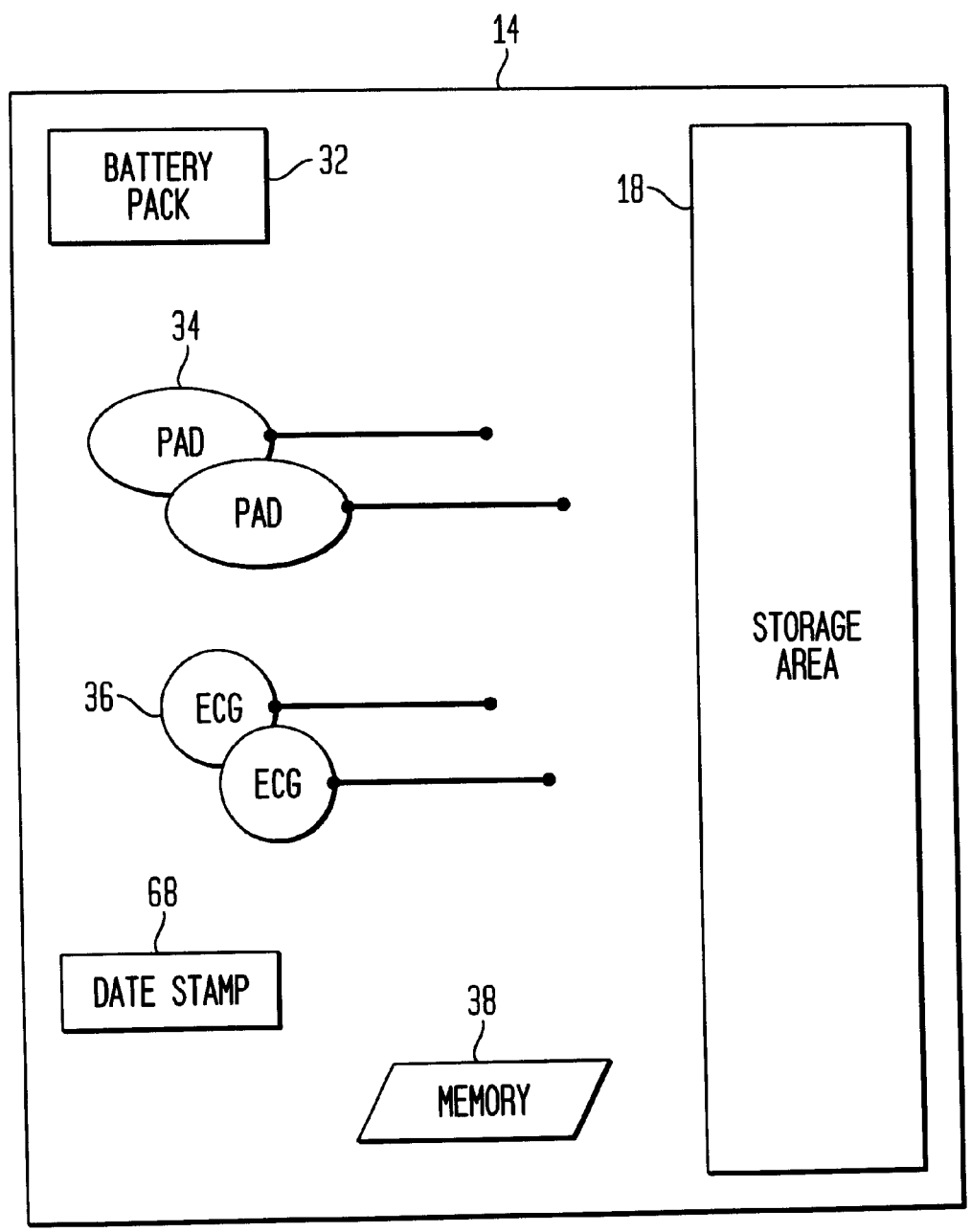
FIG. 3 is a schematic block diagram of the module of FIG. 2.

As shown in FIG. 2, items containable by the supply module 14 include pads, ECG leads, gloves, a CPR barrier mask, scissors, PCMCIA cards and batteries, as well as any other components or supplies desired to be included by the operator or manufacturer. The specific selection of components depends on the intended use of the supply module. The supply module 14 typically is formed from an outer shell 16 in which compartments 18 are formed for receiving the above items. Shell 16 is typically formed of a hard plastic. Tie downs 20 within the storage compartment 18 can be used to retain securely the supplies within the compartments 18. The supply module 14 may be disposable, and discarded after use, or may be returned to the manufacturer for refurbishment after use or after expiration.

The supply module 14 may be hermetically or otherwise sealed by a layer 22 to ensure the supplies remain fresh for as long as possible and to prevent the supplies from being contaminated. Layer 22 may be formed of plastic or other material and is adhered or attached to the periphery of the supply module 14 to provide the desired seal. The layer 22 is removable, such as by peeling, to allow access to the supplies. The layer 22 may be opaque or clear. One or more electrical connectors 24 may be formed through, printed on or formed by the layer 22 such that upon removal of the layer 22 to access the contents of the supply module 14, the defibrillator 10 is automatically turned on.

Figure 4:
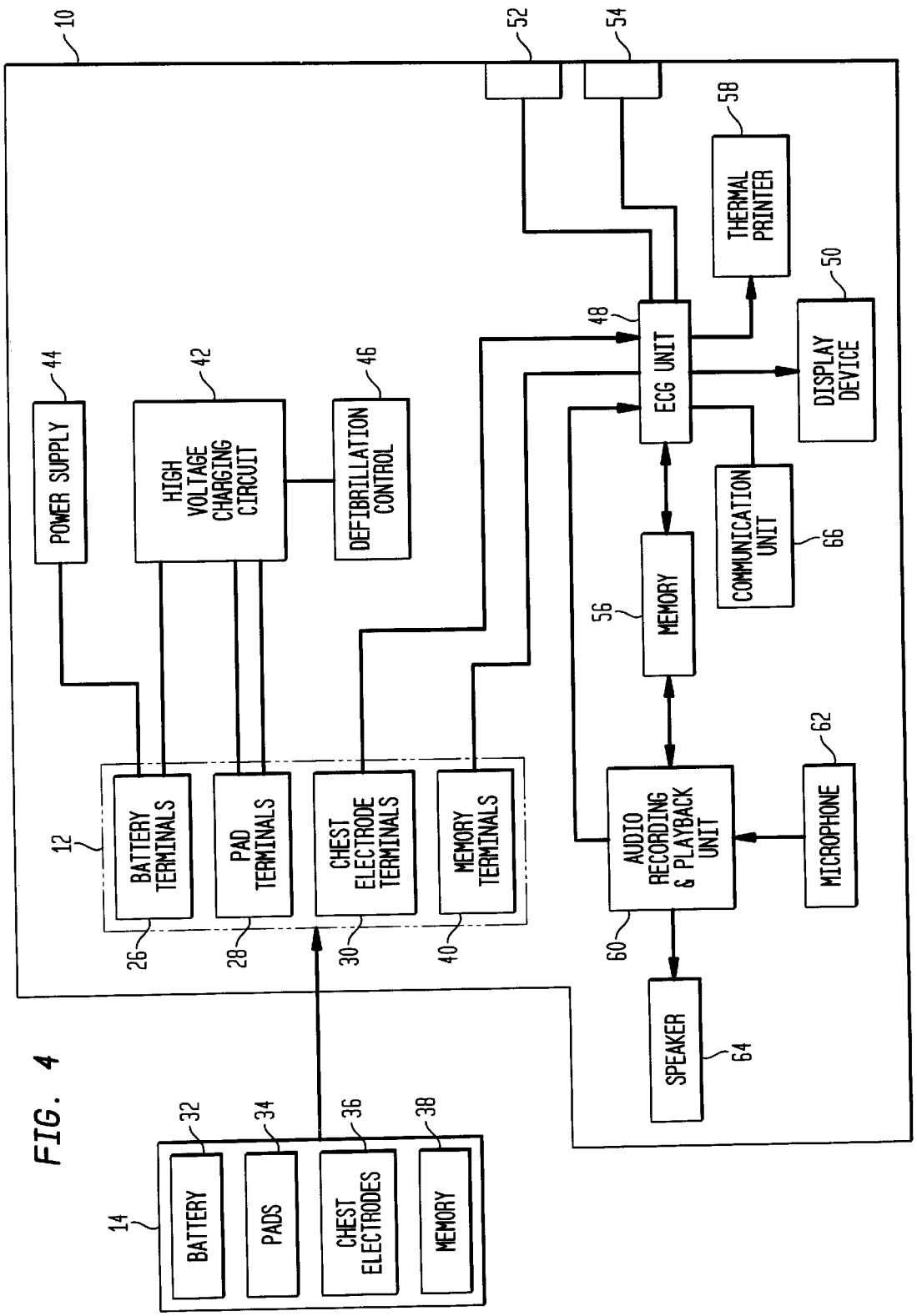
FIG. 4 is a functional block diagram of the defibrillator of FIG. 1.

The supply module 14 preferably is electrically interconnected to the defibrillator 10 via battery terminals 26, pad terminals 28, chest electrode terminals 30, memory terminals 40 and any other terminals necessary or desirable for electrically interconnecting the supply module or items contained within the supply module to defibrillator 10. As shown in FIG. 4, battery terminals 26 provide an interconnection between the battery 32 in module 14 and defibrillator 10. Battery 32 supplies power to defibrillator 10. Pad terminals 28 provide an interconnection between the pads 34 and defibrillator 10 and chest electrode terminals 30 provide an interconnection between the chest electrodes 36 and defibrillator 10. Where the supply module 14 is provided with a memory 38, communication between the memory 38 and the defibrillator 10 may take place over memory terminals 40.

Referring generally to FIG. 4, socket 12 includes a plurality of battery terminals 26 for attachment to the rechargeable battery 32. Battery pack 32 preferably includes one or more batteries capable of providing power to the defibrillator 10 for several hours of operation. As illustrated, battery pack 32 is electrically coupled to high voltage charging circuit 42 via battery terminals 26 when the supply module 14 is coupled to the socket 12 on the defibrillator 10. Upon connection and on demand, battery 32 supplies charge to a large capacitor contained within high voltage charging circuit 42 utilized to store the large charge required to defibrillate a patient suffering from sudden cardiac arrest. The high voltage charging circuit 42 is electrically connected to a pair of pads 34 utilized to deliver a defibrillating shock to the patient via pad terminals 28. The delivery of the defibrillating shock is controlled by defibrillation control 46. Battery pack 32 is further electrically coupled via battery terminal 26 to power supply 44, which supplies power to the control and monitoring circuitry within the defibrillator 10.

Still referring to FIG. 4, defibrillator 10 further includes electrocardiogram (ECG) unit 48, which controls the monitoring functions of the defibrillator 10. From the following description of ECG unit 48, those skilled in the art will appreciate that the ECG unit 48 may be implemented utilizing a conventional microprocessor and support circuitry, or alternatively, an application-specific integrated circuit (ASIC). The ECG unit 48 receives ECG data from the patient through the chest electrodes 36 connected to the defibrillator 10 at chest electrode terminals 30. The chest electrodes 36 are preferably disposable electrodes and are preferably coated with a conductive gel to establish a good electrical contact with the patient. The ECG data received from the patient is temporarily buffered in an ECG data buffer within ECG unit 48 and displayed in real-time to the operator of defibrillator 10 with display device 50. The ECG data is preferably displayed in the form of a conventional ECG waveform trace, and may be displayed in conjunction with additional information extracted from the ECG data, such as the patient's instantaneous pulse rate.

The supply module memory 38 on the supply module 14 is connected to the ECG unit 48 via memory terminal 40. The supply module memory 38 may be configured to store information transmitted from the defibrillator 10 to the supply module 12, such as ECG data, audio data or other information relating to the sequence and timing of events occurring during operation of the defibrillator. This information can be used by a number of people, such as the defibrillator manufacturer in connection with designing future defibrillators, or by medical personnel while assessing the performance of the rescue team using the defibrillator. The supply module memory 38 may also be configured to store information for transmission to the defibrillator 10, such as software upgrades, codes, passwords or other indicia required to activate circuitry on the defibrillator, expiration date information, or any other information necessary or desirable for proper operation of the defibrillator.

The specific type of memory used on supply module 14 depends on the intended purpose of the supply module memory 38. If the supply module memory 38 is to be read only, ROM may be used. ROM is preferable in this situation since it is possible to maintain information in ROM without connecting a source of electrical power to the ROM. Where the memory 38 is to be writable, as well as readable, random access memory (RAM) may be used. As is well known, RAM must be refreshed or otherwise maintained by an external source of electrical power. Accordingly, where RAM is to be provided, circuitry associated with refreshing and otherwise maintaining the RAM using the battery 32 as a source of power should also be provided. Optionally, two types of memory may be provided: ROM may be used to store information for transmission to the defibrillator and RAM may be provided to receive information from the defibrillator. In this situation, the supply module 14 may be configured such that the RAM is only maintained after the defibrillator 10 has transmitted information to the supply module memory 38. Implementation of the various types of memory is well within the abilities of a person of ordinary skill in the art. Optionally, the memory within the supply module could comprise a PCMCIA (Personal Computer Memory Card International Association) memory card.

Supply module memory 38 may also be useful to disseminate software, algorithms and other information to defibrillators 10. For example, updated instructions relating to operation of the defibrillator 10 or updated algorithms useful to analyze ECG waveforms may be placed in the supply module memory 38. Since each supply module has a predetermined shelf life and will eventually need to be replaced, storing software and algorithms in the supply module memory 38 enables the software and algorithms used by each defibrillator in a fleet of defibrillators to be updated without recalling the defibrillators or requiring a special installation of the new programs or data to each defibrillator. Although several uses for the memory 38 have been explained, the memory 38 is not limited to these uses, and may be used for additional tasks as well. Transfer of information between the defibrillator and the supply module memory 38 may be performed using any known protocol.

ECG unit 48 is further coupled to user controls 52, 54, such as a "mark" button 52 which is depressed by an operator to store ECG data of interest within defibrillator memory 56. Optionally, this information may be stored in supply module memory 38 as well. Indeed, any information stored within defibrillator memory 56 may optionally be stored within supply module memory 38. During treatment of a patient, the operator typically utilizes mark button 52 to record segments of ECG data sensed before and after the administration of drugs, the delivery of shocks, and other major treatment events. The collection of BCG data segments stored in memory 56 by the operator during treatment of a patient, known as a "code" summary, can be printed by the operator of defibrillator 10 on thermal printer 58 by depressing review button 54. In addition, the ECG unit 48 could store all of the patient's ECG data sensed during treatment within memory 56 in conjunction with a list of marked events for later use. Alternatively, ECG unit 48 could automatically mark events preselected by the operator, such as the delivery of shocks.

The ECG unit 48 is further coupled to an audio recording and playback unit 60 that receives audio input from a microphone 62 and presents audio output to the operator of defibrillator 10 through a speaker 64. In response to user input via control 52, 54, the audio recording and playback unit 60 sense audio data via microphone 62, digitizes the audio data, and stores the audio data within the memory 56. As will be appreciated by those skilled in the art, the audio data can be compressed prior to storage utilizing any of a number of well-known data compression algorithms in order to minimize the size of memory 56 required to store the audio data. The audio data may be stored within the memory 56 in association with the ECG data recorded in response to the same depression of the mark button 52. The audio data may also b e stored by audio recording and playback unit 60 on magnetic tape, such as radio cassette or micro cassette tape.

To facilitate the memory 56, memory 56 preferably comprises a removable and portable data storage device, such as a PCMCIA memory card; however, the memory 56 can alternatively be implemented as a nonremovable memory. In addition, the defibrillator 10 preferably includes an infrared serial port or other data communication means (not illustrated) to enable the contents of memory 56 to be directly downloaded to a computer for review and analysis.

As indicated above, items contained in the supply module 14 have predetermined shelf lives. To facilitate monitoring the remaining shelf life of the items, the supply module 14 is itself provided with a shelf life. The shelf life of the supply module 14 or the contained items may be printed on an outer surface of the supply module 14 to enable an operator or maintenance personnel to determine whether the items contained within the supply module 14 have expired.

In another aspect of the invention, electronic indicia may be provided on the supply module 14 to enable the defibrillator 10 to sense impending or actual expiration of the supply module 14. The electronic indicia may be contained within supply module memory 38, in a separate memory on the supply module, or in an electronic circuit. When the supply module 14 is provided with electronic indicia, the defibrillator 10 may be configured to receive signals relating to the electronic indicia and use the signals during periodic self tests or upon start up to ascertain whether the expiration date on the supply module 14 has passed. If so, the defibrillator may issue an audible or visual warning indicating that the supply module needs to be replaced. The warning may be communicated using a communication unit 66 connected to a cellular or land-based telephone network, or any other network, to enable one or two way communication between the defibrillator 10 and a central station or other resource. The central station can then dispatch a repair technician or otherwise order a new supply module for the defibrillator.

The communication unit 66 may be used by the defibrillator 10 prior, during or subsequent to defibrillation. For example, the defibrillator 10 could communicate with the central station the result of a periodic self test including the status of the supply module 14, prior to defibrillation. During defibrillation, the defibrillator 10 could communicate the ECG waveform data to a doctor at the central station 10 to receive more advanced medical advice. Finally, after defibrillation, the code summary or other information may be communicated to the central station over communication unit 66.

In a further aspect of the invention, module 14 may be a training supply module containing items useful for operation of the defibrillator during training. The training supply module preferably is similar to the supply module so that the person operating the defibrillator during the training session experiences a realistic defibrillation simulation. The electronic memory of the training supply module may be configured to contain one or more training scenarios. For example, the training supply module could contain a memory having samples of ECG data, sample audio data, etc. The training supply module could pass this data to the defibrillator as part of the training exercise to simulate more accurately an actual resuscitation attempt. Once the training has been completed, the training module could be replaced with supply module 14 to render the defibrillator 10 fully supplied and ready for use.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A defibrillation system, comprising:
   an external defibrillator including:
      a replaceable supply module including pads, a battery and a container with compartments configured to contain the pads and the battery.
2. The defibrillation system of claim 1, wherein the replaceable supply module is electrically connected to the external defibrillator.
3. The defibrillation system of claim 2, wherein the defibrillator is configured to conduct a periodic test of the replaceable supply module.
4. The defibrillation system of claim 3, wherein the defibrillator further comprises a communication unit configured to communicate data regarding the periodic test of the replaceable supply module to a remote location.
5. The defibrillation system of claim 1, wherein said defibrillator is configured to monitor said supply module.
6. The defibrillation system of claim 1, wherein said supply module further contains at least one of ECG leads, gloves, a CPR barrier mask, a PCMCIA memory card and scissors.
7. The defibrillation system of claim 1, wherein said supply module comprises a memory configured to store information for transmission from the supply module to the defibrillator.
8. The defibrillation system of claim 7, wherein said information includes at least one of expiration date information, training information, code information and software information.
9. The defibrillation system of claim 1, wherein said supply module comprises a memory configured to store information including at least one of ECG data, event data and audio data.
10. The defibrillation system of claim 1, wherein:
    said defibrillation system further comprises a display;
    said replaceable supply module further comprises a memory which stores an expiration date of said replaceable supply module; and
    said defibrillator is configured to monitor the expiration date and to communicate expiration of said replaceable supply module to a user via the display.
11. A defibrillation system, comprising:
    an external defibrillator including:
       a replaceable supply module including defibrillation pads and a battery, mounted on said external defibrillator wherein an indication of the earlier of an expiration date of said pads and an expiration date of said battery is printed on said replaceable supply module visible to a user of said defibrillation system.
12. A defibrillation system, comprising:
    an external defibrillator including:
       a replaceable supply module, including pads and a battery, having an expiration date printed on a surface of said replaceable supply module visible to a user of said defibrillation system.
13. A defibrillation system, comprising:
    an external defibrillator including:
       a replaceable supply module, including: pads, a battery and a memory which stores an expiration date in machine-readable form, wherein said defibrillator is configured to recognize said expiration date.
14. The defibrillation system of claim 9, wherein said external defibrillator further comprises a communication unit which receives the expiration date of the replaceable supply module.
15. A defibrillation system, comprising:
    a defibrillator; and
    a replaceable supply module, having an expiration date of the replaceable supply module stored on the replaceable supply module, and comprising:
       defibrillation pads electrically connected to the defibrillator;
       a compartment which contains said pads; and
       a battery electrically connected to said defibrillator,
    wherein:
       said defibrillator is configured to monitor the expiration date, and
       said defibrillator further comprises a communication unit configured to communicate expiration of said replaceable supply module to a remote location.

16. A defibrillation system, comprising:

a defibrillator; and a supply module, comprising:
   compartment containing defibrillation pads electrically connected to the defibrillator,
   a battery electrically connected to the defibrillator, and
   a memory which stores an expiration date,
wherein the defibrillator is configured to issue at least one of an audible and a visual warning based on the stored the expiration date.

17. A defibrillation system, comprising:

a defibrillator which supplies an electrical charge; and a replaceable supply module comprising:
   pads to connect said electrical charge to a patient,
   a battery which powers said defibrillator, and
   a compartment which contains said pads, wherein operation of said defibrillator is initiated by inserting said replaceable supply module in said defibrillator.

18. A defibrillation system, comprising:

an external defibrillator; and a replaceable supply module including pads, a battery and a container with,, compartments configured to contain the pads and the battery, the replaceable supply module electrically connected to the external defibrillator and further comprising a peelable top surface, and wherein operation of the defibrillator is initiated by peeling the peelable top surface.

* * * * *